US012613843B1

(12) United States Patent
Orozco et al.

(10) Patent No.: US 12,613,843 B1
(45) **Date of Patent: \*Apr. 28, 2026**

(54) SYSTEM AND METHOD FOR SECURE MATCHING AND LINKING OF DATA ELEMENTS ACROSS INDEPENDENT DATA SYSTEMS

(71) Applicant: Verato, Inc., McLean, VA (US)

(72) Inventors: Luis V. Orozco, Vienne, VA (US); Jonathan P. Case, Cary, NC (US); Jeffrey B. Williams, Arlington, VA (US); Tara F. Figley, Morrisville, NC (US); Sean M. Pritchard, Clayton, NC (US)

(73) Assignee: Verato, Inc., McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/543,399

(22) Filed: Dec. 18, 2023

Related U.S. Application Data

(63) Continuation of application No. 15/581,956, filed on Apr. 28, 2017, now Pat. No. 11,899,632.

(51) Int. Cl.
*G06F 16/215* (2019.01)
*G06F 21/62* (2013.01)
(Continued)

(52) U.S. Cl.
CPC ........ *G06F 16/215* (2019.01); *G06F 21/6227* (2013.01); *G16H 10/60* (2018.01); *G06Q 40/08* (2013.01)

(58) Field of Classification Search
None
See application file for complete search history.

(56) References Cited

U.S. PATENT DOCUMENTS

| | | | |
|---|---|---|---|
| 6,389,429 B1 | 5/2002 | Kane et al. | |
| 7,046,994 B1 | 5/2006 | Padawer et al. | |
| | (Continued) | | |

OTHER PUBLICATIONS

Phatak, et al., Conflict Resolution and Reconciliation in Disconnected Databases; Department of Computer Science, Rutgers University, New Brunswick, NJ; pp. 1-6.
(Continued)

*Primary Examiner* — Amy Ng
*Assistant Examiner* — Anthony G Gemignani
(74) *Attorney, Agent, or Firm* — Fox Rothschild LLP

(57) ABSTRACT

A methods, systems, and devices for secure linking and matching of data elements across independent data systems of a first and a second enterprise are disclosed. The system includes a first private data system having a first private database that may include all attributes known to the first enterprise A reference data system having a reference database and is also part of the first enterprise. The reference database may contain a plurality of identity data records that only contain identity attributes that are used for resolving and verifying identities of unknown data records that are external to the reference data system. A first set of query attributes may be used determine whether a subject represented by the first set of query attributes associates uniquely with a subject of any private data record stored in the first private database. A similar comparison may be made in the reference database.

18 Claims, 6 Drawing Sheets

(51) Int. Cl.
    *G06Q 40/08*        (2012.01)
    *G16H 10/60*       (2018.01)

(56)           References Cited

U.S. PATENT DOCUMENTS

| | | |
|---|---|---|
| 7,209,911 B2 | 4/2007 | Boothby et al. |
| 7,363,325 B2 | 4/2008 | Manilos et al. |
| 7,509,326 B2 | 3/2009 | Krabel et al. |
| 7,546,286 B2 | 6/2009 | Dickinson et al. |
| 7,627,611 B2 | 12/2009 | Gusciora |
| 7,707,177 B2 | 4/2010 | Bank et al. |
| 7,788,225 B2 | 8/2010 | Fish et al. |
| 8,001,078 B2 | 8/2011 | Banks et al. |
| 8,301,593 B2 | 10/2012 | Hoffmann et al. |
| 8,589,510 B2 | 11/2013 | Jackson |
| 8,892,571 B2 | 11/2014 | Friedlander et al. |
| 9,129,046 B2 | 9/2015 | Bess et al. |
| 9,195,725 B2 | 11/2015 | Brown et al. |
| 9,286,369 B2 | 3/2016 | Pei et al. |
| 9,519,798 B2 | 12/2016 | Egorov et al. |
| 9,892,231 B2 | 2/2018 | Vdovjak |
| 10,249,385 B1 | 4/2019 | McNair et al. |
| 10,340,033 B2 | 7/2019 | Bucur et al. |
| 10,657,613 B2 | 5/2020 | Bucur et al. |
| 11,114,185 B1 | 9/2021 | Malec et al. |
| 2003/0055828 A1 | 3/2003 | Koch et al. |
| 2004/0148290 A1 | 7/2004 | Merenda et al. |
| 2005/0240569 A1 | 10/2005 | Cheng et al. |
| 2006/0123010 A1 | 6/2006 | Landry et al. |
| 2006/0271401 A1 | 11/2006 | Lassetter et al. |
| 2008/0208797 A1 | 8/2008 | Witzke et al. |
| 2009/0210453 A1 | 8/2009 | Vetter et al. |
| 2010/0169348 A1 | 7/2010 | Maro et al. |
| 2010/0312766 A1 | 12/2010 | Horn |
| 2011/0039249 A1 | 2/2011 | Packard et al. |
| 2011/0066446 A1 | 3/2011 | Malec et al. |
| 2011/0246237 A1* | 10/2011 | Vdovjak ................ G16H 10/60 705/3 |
| 2012/0158807 A1 | 6/2012 | Woody et al. |
| 2012/0233209 A1 | 9/2012 | Cheng et al. |
| 2012/0233530 A1 | 9/2012 | Stroe et al. |
| 2013/0110845 A1* | 5/2013 | Dua ...................... G06F 16/215 707/769 |
| 2014/0040313 A1 | 2/2014 | Shami et al. |
| 2014/0136440 A1 | 5/2014 | Ahmed et al. |
| 2015/0025913 A1 | 1/2015 | Friedlander et al. |
| 2015/0149488 A1 | 5/2015 | Ebaugh et al. |
| 2015/0213380 A1 | 7/2015 | Cooper et al. |

OTHER PUBLICATIONS

Sauleau et al., "Medical record linkage in health information systems by approximate string matching and clustering," BMC Medical Informatics and Decision Making (2005); 5(32): 1-13.

Verato, Inc., "Verato Linktm," Verato Identity Integrity, 2015 (2 pages).

Verato, Inc., "Verato Validatetm," Verato Identity Integrity, 2015 (2 pages).

* cited by examiner

SYSTEM AND METHOD FOR SECURE MATCHING AND LINKING OF DATA ELEMENTS ACROSS INDEPENDENT DATA SYSTEMS

RELATED APPLICATIONS

The application is a continuation of U.S. patent application Ser. No. 15/581,956, filed Apr. 28, 2017, currently pending, the disclosure of which is incorporated in its entirety herein by reference.

FIELD OF THE DISCLOSURE

This invention relates to the field of information sharing among computer systems, specifically real-time, Web services, and batch interactions that are conducted between two or more systems within a single heterogeneous enterprise or two or more systems across two or more heterogeneous enterprises for matching and linking subject data records despite variations in the attributes used to describe the subject in different systems and enterprises.

BACKGROUND

Currently, when a record containing attributes that pertain to a given person or entity (i.e., the subject) are presented to a data system, that data system uses a matching algorithm to determine whether or not its data base contains a corresponding record. Depending on the type of matching algorithm used to compare the attributes from the presented record to the reference records in the second system, there are several outcomes that could occur. For example, if all the attributes pertaining to the subject that were in the presented record match the attributes in the reference database, the data transaction can be processed. However, and by way of example only, if the matching algorithms determine there is not a match, incorrectly resulting in a false negative. Such a scenario could result in the data transaction being incorrectly rejected; or possibly incorrectly creating duplicate records for the same subject. Alternatively, the matching algorithms might incorrectly determine that the attributes do match, when in fact the two subjects are not the same person or entity, resulting in a false positive.

SUMMARY OF THE INVENTION

Methods, systems, and devices that enable separate enterprises to link internal records associated with subjects, across the enterprises, on an enduring basis when the subjects are identified by attributes, are disclosed.

More particularly, methods, systems, and devices for the secure linking and matching of data attributes or elements across independent data systems of a first and a second or more enterprises are disclosed. The disclosed systems include by way of example only, a first private data system having a first private database and is part of the first enterprise. The first private database may include one or more private data records that uniquely represent subjects known to the first enterprise and having been provided by a second enterprise. The private data records contained in the first private data system contain private attributes related to the subject of the private data record. One of the private attributes stored in the private data record is the private data record ID attribute. The private data record may pertain to one subject, which may be among other things an individual, a patient, a group, or a business entity.

The disclosed systems also include a reference data system having a reference database that is also part of the first enterprise. The reference database may include all reference data records that represent all subjects known to the first enterprise. The reference data records contained in the reference data system contain attributes related to the subject of the reference data record by the first enterprise. One of the reference attributes stored in the reference data record is the reference data record ID attribute. The reference data record will pertain to one subject, which may be among other things an individual, a patient, a group, or a business entity. In an aspect, the reference database may contain a plurality of identity data records that only contain identity attributes that are used for resolving and verifying identities of unknown data records that are external to the reference database and associated reference data system.

The first private database may be, for example, configured to receive a first set of query attributes from a second enterprise wherein the query attributes represent a given subject, or the first set of query attributes could be from a data system associated with the second enterprise. Using the received query attributes, the first private database contained in the first enterprise may determine whether the subject represented by the first set of query attributes associates uniquely with any subject represented by a private record ID attribute or any other attribute or attributes stored in the first private database. The subject represented by first set of query attributes is associated uniquely with a subject represented by a selected private data record when the query attributes can be matched to attributes in the selected private data record, to the exclusion of all other potential combination of attributes in other private data records in the private database. This matching can be accomplished deterministically using the private record ID attribute or by matching other attributes such that one private data record is uniquely and exclusively similar, or by other matching algorithms.

On a condition that the subject of a private data record in the first private database is associated uniquely with the subject represented by the first set of query attributes, the first set of query attributes, if different from the ones already known in the private data record, may be stored in the first private database as additional attributes that represent the private data record. In return, a message may be sent to the second enterprise containing the selected private record ID attribute and/or the one or more attributes stored in the first private database that represents the selected subject.

In one implementation, a method may include a step of receiving, at a first private data system of a first enterprise, a first query message sent from a second enterprise comprising a first set of query attributes representing a subject, wherein the first private system includes a first private database that contains all private attributes known to the first enterprise and provide by the second enterprise regarding private data records contained in the first private data system, and wherein each attribute has been previously added to a private data record, pertaining to a subject.

In another implementation, a method may include a step of receiving, at a reference data system of a first enterprise, a first query message comprising a first set of query attributes representing a subject, wherein the reference data system includes a reference database that contains all known attributes regarding data records contained in any data system that is in communication with the reference database, and each may have been previously matched to a reference data record, pertaining to a subject, having a reference identifier (ID) attribute in the reference data system. The method may also include a step of determining whether the subject represented by the first set of query attributes associates uniquely with any subject represented by a reference ID attribute stored in the reference database.

On a condition that a subject represented by a selected reference record ID in the reference database associates uniquely with the subject represented by the first set of query attributes, the method may also include a step of sending, to a first private data system in communication with the reference data system and including a first private database, a second query message comprising a first set of combined attributes representing the subject and containing by way of example only the query attributes and the selected reference ID attribute. More specifically, the combined attributes may comprise the first set of query attributes and at least one additional attribute stored in the reference database associated with the selected reference record ID, wherein the first private database includes all attributes known to the first enterprise regarding data records contained in the first data system, wherein each attribute has been previously matched to a private data record, pertaining to a subject, having a private record ID in the first private data system. The method may also include a step of determining whether the subject represented by the selected reference ID attribute is associated uniquely with the subject represented by any private ID attribute stored in the first private database.

On a condition that the subject represented by the selected private ID attribute in the private database associates uniquely with a subject represented by the selected reference ID attribute, the method may include a step of storing the first set of query attributes in the first private database, and returning, to the second enterprise, the selected private ID attribute. The selected private ID attribute may, for example, enable the second enterprise to request data records pertaining to a subject directly from the first enterprise without further verification of the selected subject's identity.

DETAILED DESCRIPTION OF THE PREFERRED EMBODIMENTS

Figure 1A:
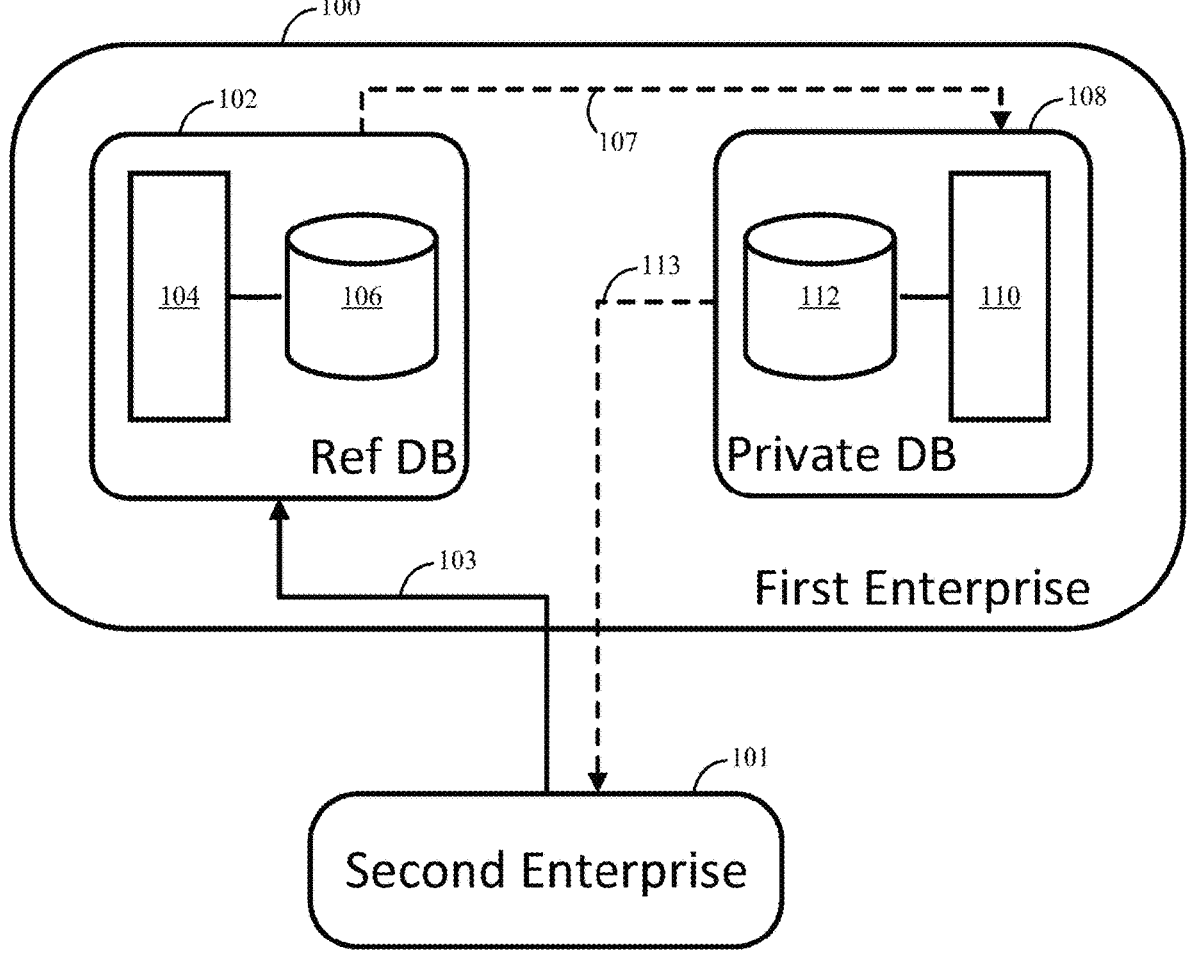
FIG. 1A is a block diagram showing example data systems for use in implementing the disclosed embodiments.

Embodiments of the present invention are not limited to the particular methodology, uses, and applications described herein, as these may vary. It is also to be understood that the terminology used herein is used for the purpose of describing particular embodiments only, and is not intended to limit the scope of all embodiments of the present invention. It must be noted that as used herein and in the appended claims, the singular forms "a," "an," and "the" include the plural reference unless the context clearly dictates otherwise. Thus, for example, a reference to "an element" is a reference to one or more elements, and includes equivalents thereof known to those skilled in the art. Similarly, for another example, a reference to "a step" or "a means" is a reference to one or more steps or means and may include sub-steps or subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Reference will now be made in detail to the preferred embodiments of the invention, examples of which are illustrated in the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art.

Unless defined otherwise, all technical and scientific terms used herein have the same meanings as commonly understood by one of ordinary skill in the art to which this invention belongs. Preferred methods, techniques, devices and materials are described although any methods, techniques, devices, or materials similar or equivalent to those described may be used in the practice or testing of the present invention.

All patents and other publications discussed are incorporated herein by reference for the purpose of describing and disclosing, for example, the methodologies described in such publications that might be useful in connection with the present invention. These publications are provided solely for their disclosure prior to the filing date of the present application. Nothing in this regard should be construed as an admission that the inventors are not entitled to antedate or otherwise remove any such publication or patent as prior art for any reason.

It would be advantageous to have a system that links records between institutions wherein the records at one institution are stored referencing a subject, by way of illustration for this disclosure only a patient, with attributes pertaining to that patient that are different, either through error, natural variations in time, etc., than records in a different system within either the same institution or another institution. Similarly, it would be advantageous if there were a data system that could link records associated with a given subject whose attributes are stored in a loyalty system in one retail organization, with the marketing attributes pertaining to that same subject from an alternate source, wherein the attributes used to describe the subject may be completely different, i.e., the attributes from the two separate sources cannot be compared directly, but the combination of the two sets of attributes associates uniquely with a single individual in the population with a very high degree of certainty because no other subject in the larger population of potential individuals could have the same set of attributes, errored or not.

Further, it would be advantageous to have a system that allows an institution to use the statement of a linkage, or the establishment of a link, between two records as a mechanism to de-duplicate those records wherein those records associate uniquely with each other, and the enterprise seeks to assign them a single common reference point and/or identifier for future reference, while collapsing the underlying record content about the subjects together, preferably into a single record. Finally, it would be advantageous to have a system that allows an institution possessing private attributes, such that the institution does not want other institutions to have access to its attribute content (wherein examples include insurance benefit card ID numbers, enterprise ID references, or non-traditional identifying attributes). It would be advantageous to allow such institutions to retrieve such content on an enduring basis with a high degree of confidence that, despite variations in the attributes due to errors, natural variations, or changes in data governance, that linkage of the subject of the record and the private attribute(s) endures with a very high degree of certainty.

As used in this document, a subject of a data record is the person, individual, group, entity, or thing (whether tangible or intangible) that the data record pertains to. For example, in the context of health data systems, a subject may be a patient or insurance policy holder. In this example, the subject may also be a doctor, hospital, or insurance company.

As used in this document, the term "associate uniquely", "associates uniquely", and similar variants means, with regard to data records in a data system, that the subject of a particular data record is uniquely identified to be the same as the subject of another data record (or query) because the attributes in one record can be shown to be representative of the subject of the other record through combinations of matching techniques, despite variations in the attributes, and to the exclusion of the subjects of all other subjects represented by the attributes stored in their data records.

As used in this document, the term "private" means a service or system that is provided for exclusive use by an enterprise or a group of enterprises and is not directly accessible over a public network by other enterprises. As used in this document, the phrase "private database" means a database provided to an enterprise or group of enterprises and for exclusive use by that enterprise or group of enterprises. A "private data system" is a data system that includes a private database and also includes a processor and other hardware and software elements used to implement the methods disclosed below.

As used in this document, the term "reference database" means a database provided to any enterprise or group of enterprises that subscribes to or otherwise has access to the database. The reference database is intended to be a comprehensive database of all known or nearly-all known or publicly available or purchasable data regarding subjects as discussed herein, and could include by way of example only persons within a country, state, region, or other political subdivision. A "reference data system" is a data system that includes a reference database and other hardware and software elements used to implement the methods disclosed below.

As used in this document, the term "private attribute" or "private attributes" means one or more attributes that are stored in a private database for the private use of the enterprises who have access to the private data system. Private attributes are stored such that they cannot be accessed by systems or processes that have access to the reference data system unless they are permitted by the enterprise from which the private attributes are provided.

In an example implementation, shown in FIG. 1A, data record subject association capabilities between organizations may be used, for example, to support querying for documents or patients across different organizations, and could include for example first enterprise 100 and second enterprise 101. To search for and associate identity data in the absence of a national identifier, identity matching may use, for example, a reference data system 102 and a private data system 108. Reference data system 102 includes a reference processor 104 and a reference database 106. Similarly, private data system 108 includes private processor 110 and private database 112.

In operation, a query 103 from second enterprise 101 may be received at reference processor 104. The query 103 may include a number of query attributes that describe a subject of a data record sought by the second enterprise 101. Reference processor 104 queries the reference database 106 with the query attributes to find a data record pertaining to the subject represented by the query attributes in the reference database 106, i.e., that associates uniquely with the subject of the query attributes. If a data record pertaining to a subject that associates uniquely with the subject of the query attributes is located, the reference processor 104 combines the query attributes with one or more of the attributes associated with the selected or located data record (and the subject to which the data record pertains). These combined attributes are sent to the private database through a query 107. The private processer 110 queries the private database 112 using the combined attributes to find or select a private data record pertaining to a subject that identifies uniquely with the subject represented by those combined attributes. If a private data record is found or selected pertaining to such a subject, the selected private data record pertaining to the subject may include a private record identifier (ID) attribute. One or more of the combined attributes, including the selected private record ID attribute may be sent back to the second enterprise 101 in a return message 113.

If no data record is located in the reference database 106 that associates uniquely with the subject of the query attributes, the reference data system 102 sends only the query attributes to the private data system 108 in query 107. The private processor 110 queries the private database 112 using the query attributes to find or select a private data record pertaining to a subject that associates uniquely to the query attributes. If a private data record is found or selected pertaining to such a subject, the selected private data record pertaining to the subject may include a private record identifier (ID) attribute. One or more of the attributes, including the selected private record ID attribute may be sent back to the second enterprise 101 in a return message 113.

Figure 1B:
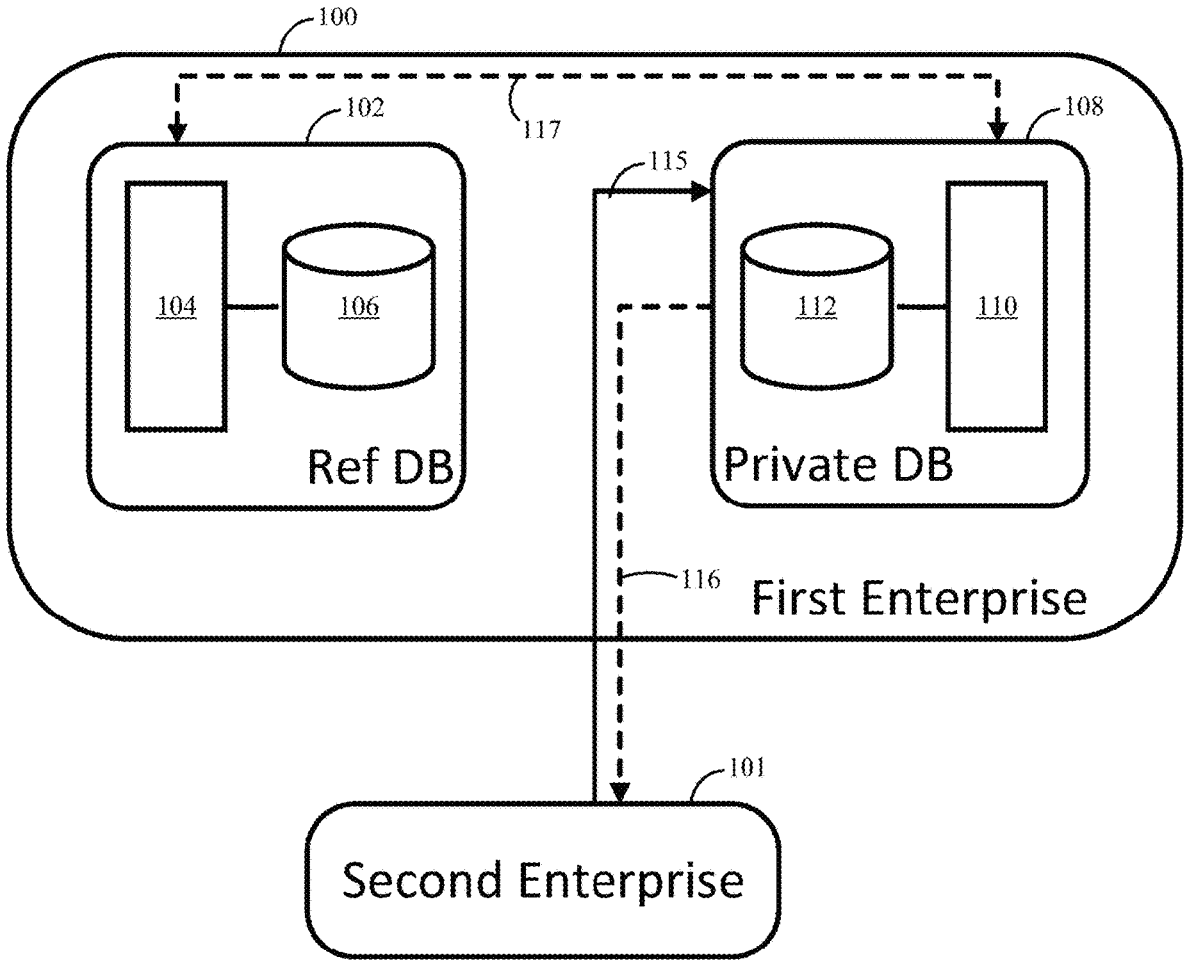
FIG. 1B is a block diagram showing example data systems for use in implementing the disclosed embodiments.

In an alternative embodiment shown in FIG. 1B, the query 115 sent from the second enterprise 101 and containing the query attributes may be received by the private data system 108. The private processor 110 uses the private attributes to query the private database 112 to find or select a private data record pertaining to a subject that associates uniquely to the query attributes. If a private data record is selected or found that pertains to such a subject, the selected private data record pertaining to the subject may include a private record identifier (ID) attribute. One or more of the attributes, including the selected private record ID attribute may be sent back to the second enterprise 101 in a return message 116.

If no private record is found or selected, the private data system 108 may send the query attributes in a query 117 to the reference data system 102. Reference processor 104 queries the reference database 106 with the query attributes in an attempt to find or select in the reference database 106 a data record pertaining to the subject represented by the query attributes, i.e., that associates uniquely with the subject of the query attributes. If a data record pertaining to a subject that associates uniquely with the subject of the query attributes is located or selected, the reference processor 104 combines the query attributes with one or more of the attributes associated with the located or selected data record (and the subject to which the data record pertains). These combined attributes are sent back to the private database through a query 117. The private processer 110 queries the private database 112 using the combined attributes to find or select a private data record pertaining to a subject that associates uniquely with the subject represented by the combined attributes. If a private data record is found or selected pertaining to such a subject, that selected private data record pertaining to the subject may include a private record identifier (ID) attribute. One or more of the combined attributes, including the selected private record ID attribute may be sent back to the second enterprise 101 in a return message 116.

Figure 1C:
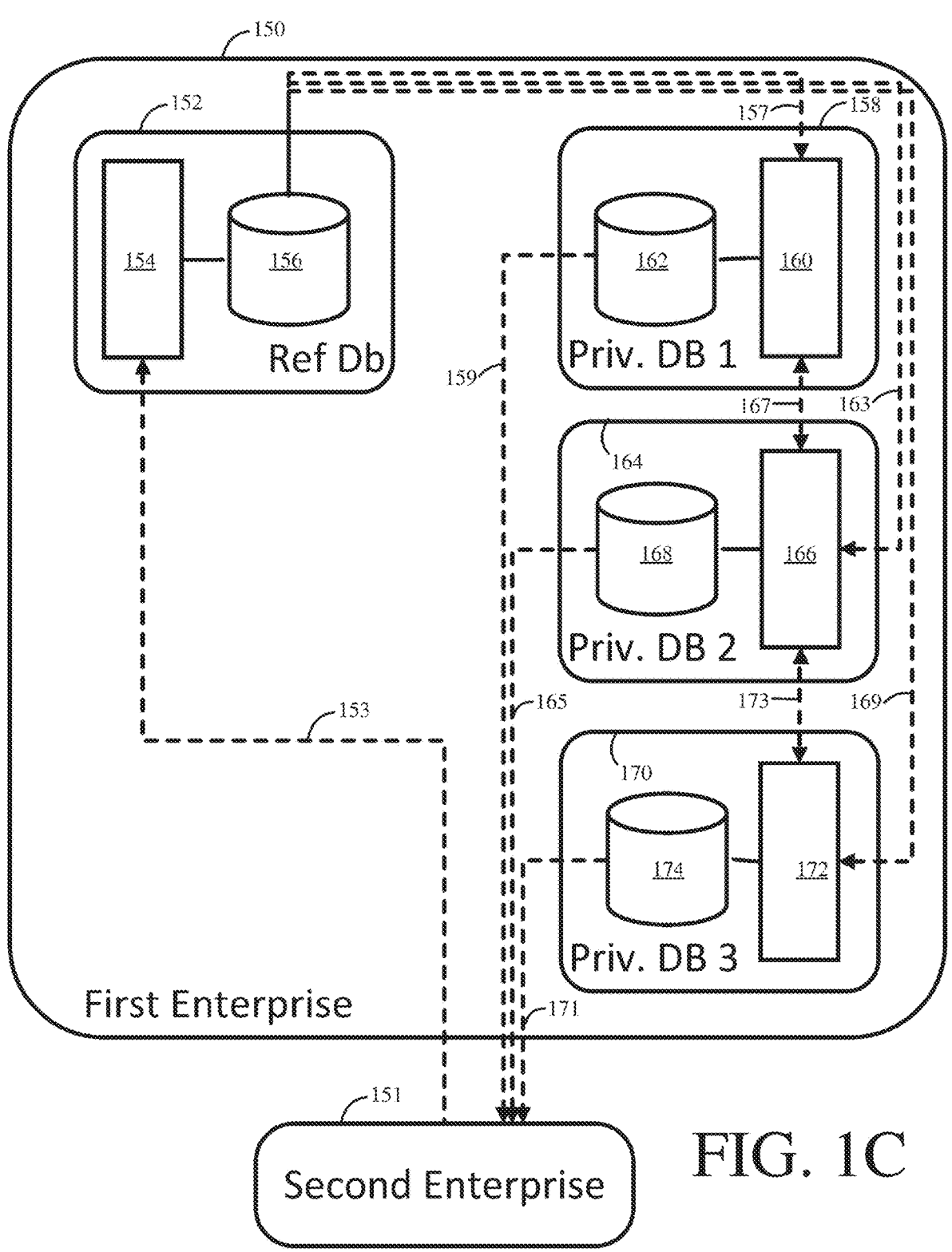
FIG. 1C is a block diagram showing example data systems for use in implementing the disclosed embodiments.

Referring now to FIG. 1C, data record subject association capabilities between organizations may be used, for example, to support querying for documents or patients across different organizations, for example first enterprise 150 and second enterprise 151. The first enterprise 150 including a reference data system 152 and multiple private data systems 158, 164, 170. The reference and private data systems shown in FIG. 1C are similarly constructed to private data system 108, shown in FIG. 1A. The reference data system 152 includes a reference processor 154 and a reference database 156. Each private data system includes a private processor 160, 166, 172, and a private database 162, 168, 174, respectively. Although three such data systems are shown in FIG. 1C, any number may be present depending on the implementation desired by the first enterprise 150.

In operation, a query 153 from second enterprise 151 may be received at reference processor 154. The query 153 may include a number of query attributes that describe a subject of a data record sought by the second enterprise 151. Reference processor 154 queries the reference database 156 with the query attributes to find or select a data record pertaining to the subject represented by the query attributes in the reference database 156, i.e., that associates uniquely with the subject of the query attributes. If a data record pertaining to a subject that associates uniquely with the subject of the query attributes is located or selected, the reference processor 154 combines the query attributes with one or more of the attributes associated with the located or selected data record (and the subject to which the data record pertains). These combined attributes are sent to the private databases through one or more queries 157, 163, 169. One or more of private processers 160, 166, 172 queries the respective private databases 162, 168, 174 using the combined attributes to find a private data record pertaining to a subject that identifies or associates uniquely with the subject represented by those combined attributes. In the case of private data system 158, the private processor 160 queries the private database 162 to find subjects that associate uniquely. In private data system 164, the private processor 166 queries private database 168 to find subjects that associate uniquely; and in private data system 170, the private processor 172 queries the private database 174 to find subjects that associate uniquely. Private databases 162, 168, 174 may also send queries 167, 173 to each other for purposes of subjects that associate uniquely. If a private data record is found or selected pertaining to such a subject, the selected private data record pertaining to the subject may include a private record identifier (ID) attribute. One or more of the combined attributes, including the selected private record ID attribute, may be sent back to the second enterprise 151 in one or more return messages 159, 165, 171.

Each private database may be associated with a separate or independent unit, enterprise, or group that elects to operate its own private database but allow other units, groups, or enterprises to share or make use of the data in their private database. By way of example only, the first enterprise 150 may be a health network, and each of the private data systems 158, 164, 170 may belong to individual hospitals or practice groups within the health network (i.e. first enterprise 150).

Figure 2:
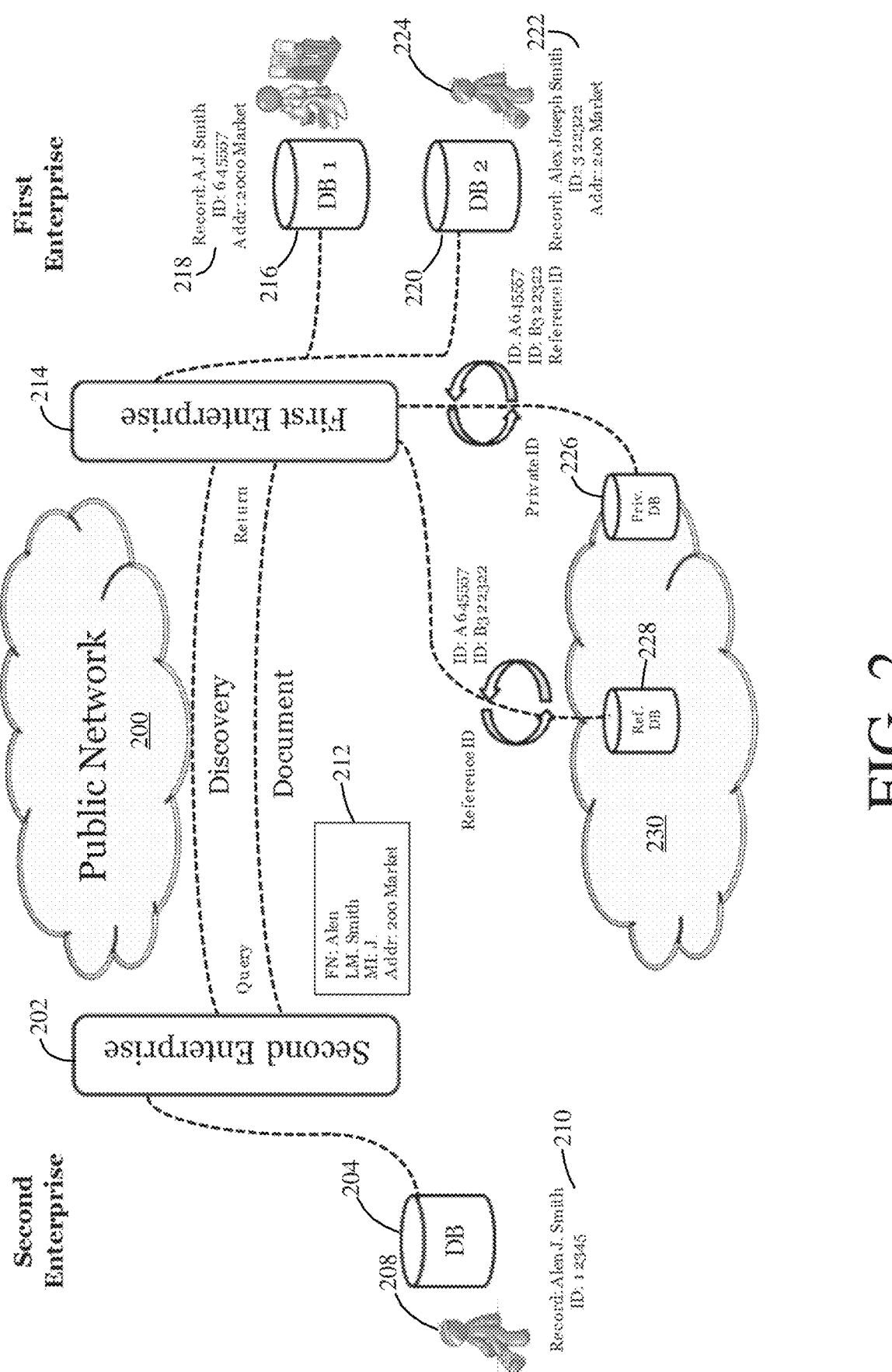
FIG. 2 is a system diagram showing an example embodiment.

In an example implementation in the healthcare industry, shown in FIG. 2, a patient discovery service interface specification may provide patient arbitration capabilities between organizations to support querying for documents across different organizations, for example second enterprise 202 and first enterprise 214. To search for patient data in the absence of a national identifier, second enterprise 202 may use, for example, a set of attributes 212 known to second enterprise 202, sent in the form of query, to identify or select the record it is seeking from the first enterprise 214. The attributes can be used to query one or both of a private database 226 and a reference database 228, which may be in a cloud implementation via network 230 to identify a record housed by the first enterprise 214. Although depicted here in the interest of simplicity as databases, private data base 226 is part of a private data system, not shown in FIG. 2 but similar to that disclosed in FIGS. 1A, 1, and 1C. Similarly, reference database 228 is part of a reference data system, not shown in FIG. 2 but similar to that disclosed in FIGS. 1A, 1B, and 1C.

In an example, a system may be designed such that one or more data systems within an enterprise (e.g., database 216, 220 of first enterprise 214 and/or database 204 of second enterprise 202) may be connected to a reference data system. Additionally, the data systems of the first enterprise 214 may be connected to one or more private data systems. For purposes of simplicity, data systems are shown on FIG. 2 as databases. It is understood that data systems may also include processors and other hardware and software as appropriate for the operation of that data system. The implementations of the present disclosure are not limited in this regard.

With regard to FIG. 2, two organizations are shown (second enterprise 202 and first enterprise 214) that wish to determine if they both have medical records for a particular individual. In this use case, second enterprise 202 utilizes a public network 200 to send requests to first enterprise 214. For example, second enterprise 202 may request information related to subject 208, whom it knows as Alen J. Smith and is assigned patient identifier ("ID"): 12345. When second enterprise 202 asks the question across the public network 200, it sends along Alen J. Smith's patient ID 210 as it exists in enterprise database 204 of second enterprise 202. This could be very problematic because the first enterprise 214 may have elected to use Alen's social security number (SSN) or some other number, and thus the two identifiers do not match, and the records pertaining to Alen J. Smith will not be found on first enterprise 214 using patient ID 210. As an alternative, second enterprise 202 may send attributes of patient 208 known to it for the purpose of matching (or linking) records held by first enterprise 214.

A private database 226 may be installed for each organization, enterprise, or group. Enterprises may set up the private database 226 using import files with each organization's patient IDs and demographic attributes associated with each patient ID. Each patient ID imported results in the creation of a new private identity or private ID, a unique identifier which identifies each individual patient in the enterprise. The private ID may be numerical, alphabetical, a glyph, or any combination, including hexadecimal. In an example, a row may be written to the private database that pairs a private ID to a particular patient ID within the enterprise along with demographic attributes that can be used to match to the private ID.

The private database (and data system) may be installed in a number of configurations depending on the needs of the enterprise. For example, first enterprise 214 connects to private database 226 through a connection to cloud service 230. Alternatively, private database 226 may be on a local area network or other non-public wide area network, such as an enterprise intranet.

To resolve identities, an enterprise can, for example, have access to reference database 228. Similar to private database 226, reference database 228 includes attribute information related to data subjects (e.g. patients). In contrast to private database 226, reference database 228 is populated with rich set of demographic information and data. For example, The reference database 228 may include all reference data records that represent all subjects known to the first enterprise. The reference data records contained in the reference data system contain attributes related to the subject of the reference data record by the first enterprise. One of the reference attributes stored in the reference data record is the reference data record ID attribute. The reference data record will pertain to one subject, which may be among other things an individual, a patient, a group, or even a business entity. The data in reference database 228, for example, may be sourced from public databases, purchasable databases, and other data sources that are available. By way of example only, the reference database combines all known and reasonably available information on individuals in a particular country, state, region, or other political subdivision as is relevant for the application. As an example, reference database 228 may house all public and purchasable information on United States persons.

A correlation creates a pairing between two sets of attributes and assigns a floating point value to that pairing. The floating point value may be a correlation value (or certainty) that the two patients are the same individual. A correlation value of 1.0 means that the two sets of attributes have been absolutely determined to represent the same individual. A correlation of 0.0 means there may be a zero percent certainty that the two individuals are the same. Anything between indicates a degree of certainty that may not be absolute. Reference database 228 provides the best available information on the degree to which the individuals are correlated. In implementations, attributes can be added to either the reference database 228 or the private database 226 by import or through a management console.

In the example shown in FIG. 2, second enterprise 202 submits a request across the public network 200 for first enterprise 214's records on Alen Smith. Second enterprise 202 will pass Alen Smith's patient ID but first enterprise 214 has no records for that ID. The result is that no records will be returned to second enterprise 202 unless the private database is used to assist in the information recovery. Attributes can be used to query the private and/or reference databases to find a record that associate uniquely to the patient being inquired about during the exchange between second enterprise 202 and first enterprise 214, as shown in FIG. 2.

By way of example only, second enterprise 202 initiates a request across the public network 200 to first enterprise 214 with demographic attributes 212 that identify the patient 208. For example, a doctor may utilize a data system of the second enterprise 202 to input or search for records belonging to patient 208. In some implementations, patient 208 may be identified by demographic information, such as SSN. In other implementations, the patient 208 may be associated uniquely by an identifier created by second enterprise 202.

Records may also exist in one or more data systems within the control of first enterprise 214. For example, a technician may work in a medical laboratory which has performed blood work for patient being treated at a hospital. Both the laboratory and the hospital may or may not be within first enterprise 214. In this example, database 216 may be operated by the medical laboratory and database 220 may be operated by the hospital. Each database 216, 220 using different identifiers and includes different attributes 218, 222, respectively, as shown in FIG. 2.

Either patient 208 or a doctor may know or believe that records belonging to patient 208 exist in other enterprises. In this example, patient 208 and patient 224 may be the same person. When queried using attributes 212, first enterprise 214, for example, may forward the query (either in original form or repackaged as a new query) containing attributes 212 to either reference database 228 or private database 226. Which database is queried first depends on the implementation chosen by the first enterprise 214. There are slight variations in the process depending on which database is queried first as described in more detail below in reference to FIGS. 3 and 4.

In an example, the query contains demographic attributes 212 that can be used by first enterprise 214 to identify the patient, but does not include the identifier used in second enterprise 202. One of skill in the art will recognize that, although this process is described using a healthcare example, this process can be utilized in any number of other data system applications. For example, a document may include any attributes which can be used to match a file across organizations, and in fact the document can be replaced by an electronic string of data.

In one implementation, first enterprise 214, private database 226 receives the query and examines the demographic attributes 212 included in the query to determine if there is a subject in the private database 226 that associates uniquely with the attributes in the query.

If records are not found that are associated uniquely with subject 208, private database 226 may forward the query containing attributes 212 (or repackage it into a new query) to reference database 228. Reference database 228 performs the same process but with a much richer set of data, as described above. Reference database 228 receives the query and examines the demographic attributes 212 included in the query to determine if there is an associated subject in the reference database 228. The demographic attributes 212 for patient 208 are associated uniquely with data in reference database 228 populated from public and purchasable databases, as noted above, and a correlation score is assigned to the match, as described above. If the correlation score is above a threshold, the match between attributes 212 and a reference data record in reference database 228 having the same or similar attributes is deemed to be confirmed. A return query may be sent to the private database 226. The return query may include a reference ID and associated additional demographic attributes housed in reference database 228. The additional attributes and the reference ID are queried in the private database 226 using the same process above. Because the additional attributes are from a more robust data source, i.e. reference database 228, there is a higher likelihood that the additional attributes, reference ID, and the original attributes 212 may associate uniquely with a private data record. If a private data record is associated uniquely in private database 226 having the same or similar attributes as the additional attributes, a return message is sent over public network 200 to the second enterprise 202. The return message includes the private ID and the additional attributes along with the private ID.

The reference ID of a reference data record is associated uniquely with attributes 212 in reference database 228 may be returned to private database 226 and utilized as an additional attribute in the private database once the additional attributes are associated uniquely a private data record. Thus, the reference ID is another attribute that may be used to identify records in the private database. For example, each attribute set in FIG. 2 includes at least one attribute that is different from the other two. Attributes 212 include the first name "Alen" instead of "Alex". Attributes 218 include an address of "2000 Market" instead of "200 Market" and initials "A. J." instead a full first name. The reference database 228 may have been previously queried on attributes 218 and the private data record corresponding to attributes 218 may include a reference ID. In this implementation, attributes 212 do not associate uniquely with a private data record in the private database 226 but do associate uniquely with a reference data record in the reference database 228. Upon being queried with the reference ID as an additional attribute in the return query, the reference ID may be associated uniquely with that stored in the private data record containing data related to patient 224.

Figure 3:
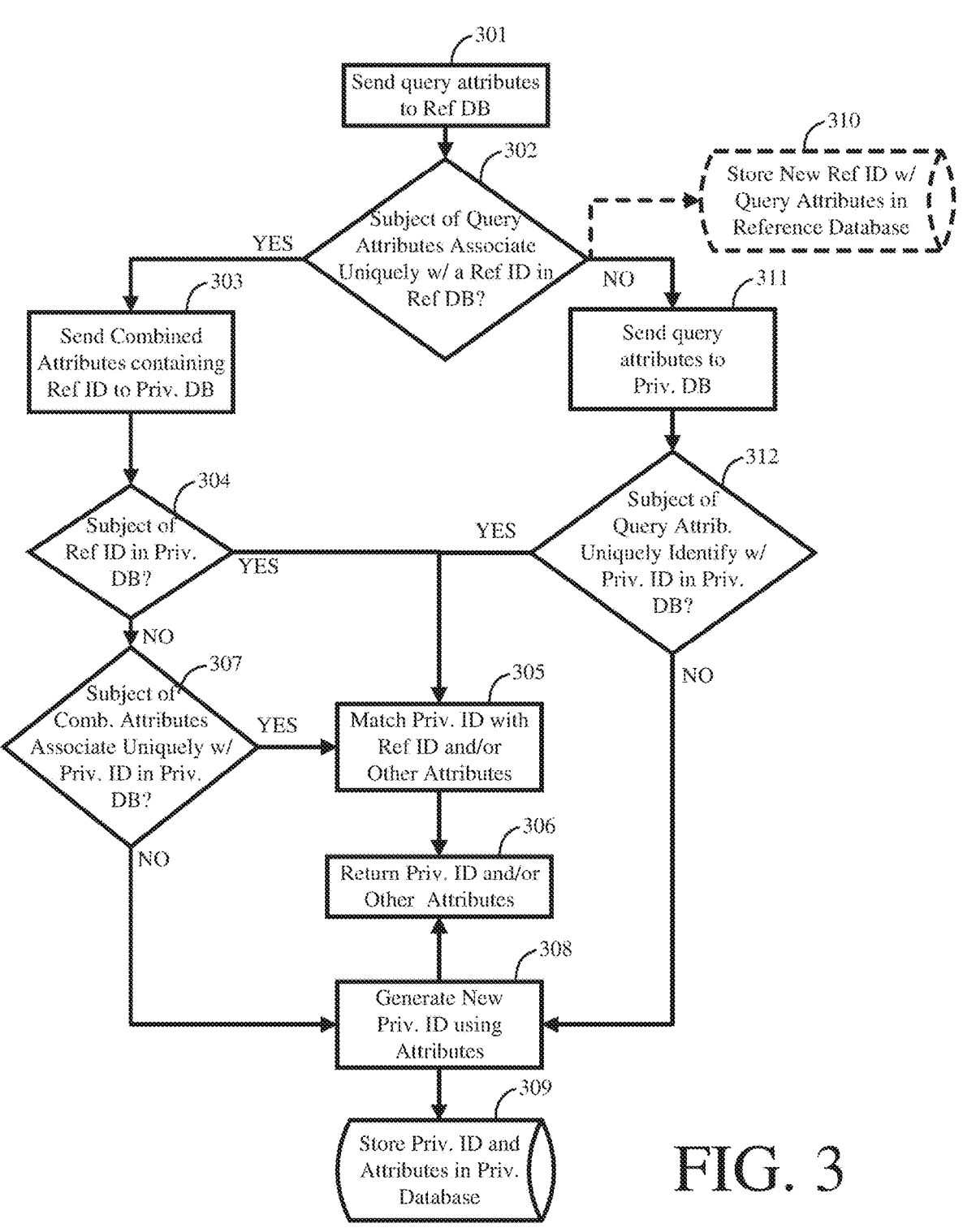
FIG. 3 is a flow diagram illustrating a method of matching and linking data records.

Referring now to FIG. 3, an example method for using the systems described in FIGS. 1A, 1i, 1C and 2 is provided. The example method of FIG. 3 may be practiced by a first enterprise in response to a query from a second enterprise. In the method, a query message sent from the second enterprise and received at a first enterprise contains one or more query attributes that are associated with or pertain to a subject, for example an individual or a patient. The implementation shown in FIG. 3 is one where query attributes that represent a subject are sent first to a reference database (step 301), for example reference database 106, 156, 228 that is part of a reference data system, for example, reference data systems 102, 152. The reference data system includes a processor and other hardware and software that can associate uniquely the query attributes to attributes stored in or associated with reference data records stored in the reference database. The reference data system determines whether the subject represented by the query attributes associates uniquely with a subject of a reference data record (step 302). If the subject of the reference data record associates uniquely with the subject of the query attributes (step 302: Yes), the reference identifier ("ID") attribute associated with or pertaining to the identified reference data record is combined with the original query attributes and with any desired additional attributes stored in the reference database and associated with or pertaining to the identified reference data record.

The combined attributes, including, for example, the reference ID attribute, are sent in a query message to a private database (step 303), for example private database 112, 162, 168, 174, 226 that is part of a private data system, for example, private data systems 108, 158, 164, 170. The private data system includes a processor and other hardware and software that can determine whether the subject represented by the combined attributes associates uniquely with a subject having attributes stored in or associated with private data records stored in the private database. The private data system determines, for example, whether the reference ID attribute is associated with a private data record in the private database (step 304). If the subject represented by the reference ID attribute associates uniquely with the subject of a private data record (step 304: Yes), the private identifier ("ID") attribute, and/or any other desired attributes, associated with the identified selected private data record is associated uniquely with the reference ID attribute and/or the combined attributes (step 305). The private ID attribute, the reference ID attribute, and/or the combined (and/or other) attributes are returned to the second enterprise (step 306).

If the subject represented by the reference ID attribute does not associate uniquely with a private data record in the private database, for example, because, for example, no private data record includes the selected reference ID attribute, (step 304: No), the private data system determines whether the combined attributes pertaining to the subject associate uniquely with the subject of a private data record (step 307). If a subject of a private data record associates uniquely with the subject represented by the combined attributes (step 307: Yes), the private identifier ("ID") attribute associated with the identified private data record is associated uniquely with the combined attributes (step 305). The private ID and the combined attributes (or the additional attributes) are returned to the second enterprise (step 306).

If the subject represented by the combined attributes does not associate uniquely with a subject of a private data record, because, for example, no data record pertaining to the subject represented by the combined attributes exists in the private data system, (step 307: No), the private data system generates a new private data record and a new private ID attribute using the combined attributes (step 308). The new private ID attribute is stored, with the combined attributes, in the new private data record in the private database (step 309). The new private ID attributes and/or the combined attributes (or other attributes) are returned to the second enterprise (step 306).

In the case where the subject represented by the query attributes does not associate uniquely so as to identify a subject represented by a reference ID attribute associated with a reference data record in the reference database (step 302: No), a new reference data record and associated reference ID attribute may optionally be generated in the reference database (step 310) that would contain at least the new reference ID attribute and the query attributes, depending on whether the first and/or the second enterprise allows attribute data to be stored in the reference database. Regardless, the query attributes are then sent to the private database (step 311). The private data system determines whether the subject represented by the query attributes associates uniquely with the subject of a private data record in the private database (step 312). If a subject of a private data record does associate uniquely with the subject represented by the query attributes (step 312: Yes), the private identifier ("ID") attribute associated with the identified private data record is associated uniquely with the query attributes (step 305) and that private data record is selected. The selected private ID attribute and, optionally, the query attributes and/or other attributes stored in the private data record are returned to the second enterprise (step 306). If a subject of a private data record does not associate uniquely with the subject represented by the query attributes (step 312: No), the private data system generates a new private data record and an associated private ID attribute using the combined attributes (step 308). The new private ID attribute is stored, with the combined attributes, in the private database (step 309). The new private ID attribute and/or the combined attributes (or other attributes) are returned to the second enterprise (step 306).

Figure 4:
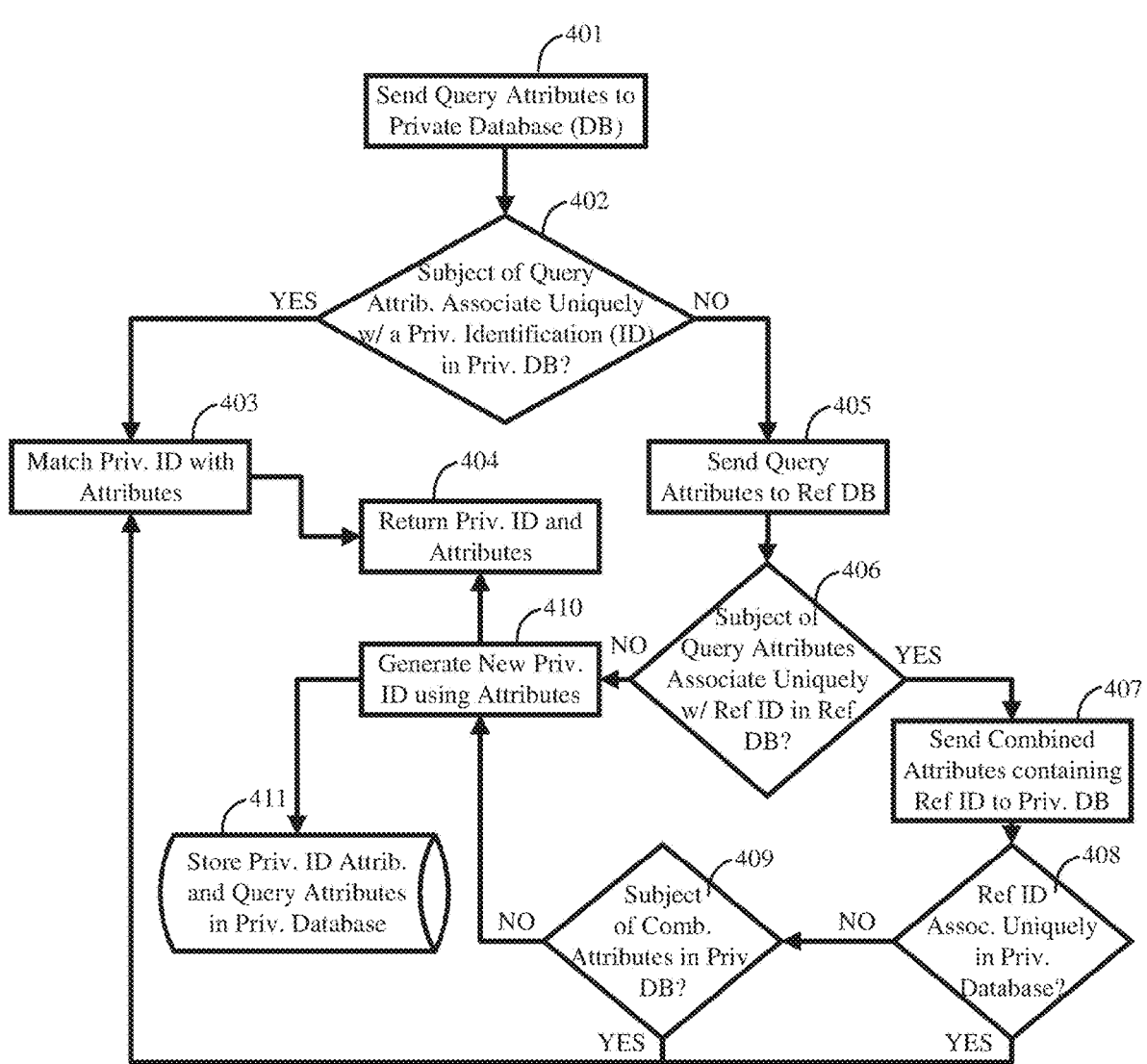
FIG. 4 is a flow diagram illustrating a method of matching and linking data records.

Referring now to FIG. 4, an example method for using the systems described in FIGS. 1A, 1i, and 2 is provided, disclosing methods practiced by a first enterprise in response to a query from a second enterprise. In the method, a query message sent from the second enterprise and received at a first enterprise contains query attributes that are associated with a subject, for example an individual or a patient. The implementation shown in FIG. 4 is one where query attributes representing a subject are sent first to a private database (step 401), for example private database 112, 162, 168, 174, 226 that is part of a private data system, for example, private data systems 108, 158, 164, 170. The query attributes are received at the private data system that includes a private database. The private data system includes a processor and other hardware and software that can associate uniquely the query attributes to attributes stored in or associated with private data records stored in the private database. The private data system determines whether the subject represented by the query attributes associates uniquely with a subject of a private data record in the private database (step 402). If a subject of a private data record does associate uniquely with the subject represented by the query attributes (step 402: Yes), the private identifier ("ID") attribute and the subject associated with the identified private data record is associated uniquely with the query attributes (step 403). The private ID attribute and/or other attributes stored in the private data record are returned to the second enterprise (step 404).

If a subject of private data record does not associate uniquely with the subject represented by the query attributes (step 402: No), the query attributes are sent in a query message to a reference database (step 405), for example reference database 106, 156, 228 that is part of a reference data system, for example, reference data systems 102, 152. The reference data system includes a processor and other hardware and software that can compare the query attributes to attributes stored in or associated with reference data records stored in the reference database. The reference data system determines whether the subject represented by the query attributes associates uniquely with a subject of a reference data record (step 406). If the subject of a reference data record does associate uniquely with the subject represented by the query attributes (step 406: Yes), the reference ID attribute associated with contained in the identified/selected reference data record is combined with the original query attributes and with any desired additional attributes stored in the reference database and associated with the identified reference data record.

The selected reference ID attribute and the combined attributes are sent in a query message back to the private database (step 407). The private data system determines whether the subject represented by the reference ID attribute associates uniquely with a subject of a private data record in the private database (step 408). If the subject represented by the reference ID attribute is associated with a subject of a private data record (step 408: Yes), the private ID attribute and the subject associated with the identified or selected private data record is associated uniquely with the reference ID and/or the combined attributes (step 403). The selected private ID attribute, the selected reference ID attribute and/or the combined (or other) attributes are returned to the second enterprise (step 404).

If the subject of the reference data record does not associate uniquely with the subject of the query attributes (step 406: No), the null result is returned to the private data system which then generates a new private data record associated with a new private ID attribute using the query attributes (step 410). The new private ID is stored, along with the query attributes, in the private database (step 411), also the new private ID and, optionally, the query attributes are returned to the second enterprise (step 404).

If the subject represented by the reference ID attribute does not associate uniquely with a subject of a private data record in the private database (step 408: No), the private data system determines whether the subject represented by the combined attributes associates uniquely with a subject of a private data record (step 409). If a subject of a private data record does associate uniquely with the subject represented by the combined attributes (step 409: Yes), the selected private identifier ("ID") attribute and the subject associated with the identified or selected private data record is associated uniquely with the combined attributes (step 403). The selected private ID and/or the combined attributes (or other attributes) are then returned to the second enterprise (step 404). If the subject represented by the combined attributes does not associate uniquely with a subject of a private data record (step 409: No), the private data system generates a new private data record associated with a new private ID attribute using the combined attributes (step 410). The new private ID attribute is stored, with the combined attributes, in the new data record in the private database (step 411). The new private ID and/or the combined attributes (or other attributes) are returned to the second enterprise (step 404).

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed is:

1. An improved data system for resolving identities of unknown data records using a reference database comprising:

a reference database of reference subjects and their associated attributes, wherein the reference database only contains a plurality of identity data records that each contain identity attributes representing one of a plurality of reference subjects, and that are used for resolving identities of unknown data records that are external to the reference data system; and a processor associated with a memory in which instructions are stored that, when executed, cause the processor to:

process a first set of query attributes of an unknown data record received from a private data system and representing a first subject, wherein the private data system includes a private database that contains one or more private data records, wherein each private data record pertains to an individual subject and each individual subject is associated with one or more private attributes representing the individual subject and contained in a given private data record;

determine whether the first set of query attributes representing a first subject resolves uniquely, using the first set of query attributes, to a selected reference subject represented by a selected reference data record contained in the reference database, wherein the selected reference data record contains one or more selected reference attributes representing the selected reference subject; and on a condition that the reference processor resolves uniquely an identity of the first subject with the identity of the selected reference subject using the first set of query attributes and the one or more selected reference attributes, return, to the external data system, a message resolving the identity of the first subject as a resolved first subject, wherein the message includes a first set of combined attributes which further include one or more of the first set of query attributes and one or more selected reference record attributes, wherein the first set of combined attributes enable the private data system to link with certainty the resolved first subject with a selected private subject of a selected private data record stored in the private data system by resolving uniquely the identity of the resolved first subject and the selected private subject.

2. The improved data system of claim 1, wherein, on a condition that the reference processor resolves uniquely an identity of the first subject with the identity of the selected reference subject using the first set of query attributes and the one or more selected reference attributes, the processor is configured to:

resolve the identity of the first subject as a resolved first subject by linking the selected reference subject with the first subject;

retrieve one or more selected reference attributes from the selected reference data record; and wherein the message resolving the identity of the first subject includes a first set of combined attributes which further include the first set of query attributes and one or more selected reference record attributes.

3. The improved data system of claim 1 wherein each reference data record in the reference database pertains to a reference subject and is comprised of all known identity data attributes associated with the reference subject as known to the reference data system, and each reference data record contains a reference record identifier (ID) attribute.

4. The improved data system of claim 3, wherein the one or more selected reference record attributes comprises the reference record ID attribute of the selected reference data record.

5. The improved data system of claim 3 wherein the one or more selected reference record attributes consists of the reference record ID attribute of the selected reference data record.

6. The improved data system of claim 4, wherein the reference record ID attribute of the selected reference data record enables the external data system to request data records pertaining to the resolved first subject directly from another data system without further resolution of the first subject's identity using the reference data system.

7. An improved method for resolving identities of unknown data records using an identity database comprising:

providing, to a first enterprise, an improved identity data system comprising an identity database of identity subjects, wherein the identity database only comprises a plurality of identity data records which each comprise a plurality of identity attributes representing one of a plurality of identity subjects, and that are used for resolving identities of unknown data records that are external to the identity data system, wherein the first enterprise includes a private data system which includes a private database that contains one or more private data records, wherein each private data record pertains to an individual subject and each individual subject is associated with one or more private attributes representing the individual subject;

receiving a first query message, sent from a second enterprise, comprising a first set of query attributes representing a first subject unknown to the first enterprise and known to the second enterprise; and on a condition that an identity of the first subject resolves uniquely to a selected identity subject represented by a selected identity data record containing one or more identity attributes contained in the identity database:

retrieving a selected identity record identifier (ID) attribute from the selected identity data record; and returning, to the first enterprise, a message resolving the identity of the first subject and including a first set of combined attributes comprising the first set of query attributes and the selected identity record ID, wherein the first set of combined attributes represent a resolved first subject, and wherein the selected identity record ID attribute from the selected identity data record contained within the identity database enables the first enterprise to link with certainty the resolved first subject with a selected private subject represented by a private data record in the private database having a plurality of private data attributes; and enable the second enterprise to request records pertaining to the selected private subject from the first enterprise without further verification the identity of the first subject.

8. The improved method of claim 7, wherein once linked by the first enterprise, the first subject, the resolved first subject, the selected identity subject, and the selected private subject are the same subject.

9. The improved method of claim 7, further comprising, after retrieving the selected identity record ID, storing, in the selected identity data record of the identity data system, all attributes contained within the first set of query attributes received from the second enterprise in the selected identity data record.

10. The improved method of claim 7, further comprising:

retrieving, with the selected identity record ID, one or more selected identity record attributes from the selected identity data record; and returning to the first enterprise, with the selected identity record ID, the one or more selected identity record attributes.

11. An improved method for resolving identities of unknown data records using an identity database comprising:

providing a reference data system comprising a reference database which only contains a plurality of identity data records which each comprise a plurality of identity attributes representing one of a plurality of identity subjects, and that are used for resolving identities of unknown data records that are external to the reference data system;

receiving, at the reference data system, a first query message from a private data system comprising a first set of query attributes representing a first subject, wherein the private data system includes a private database that contains one or more private data records, wherein each private data record pertains to an individual subject and each individual subject is associated with one or more private attributes representing the individual subject; and wherein the first query message represents a request to resolve an identity of the first subject; and on a condition that the first subject resolves uniquely with a selected reference data record, contained within the reference database, that includes one or more selected reference data attributes representing a selected reference subject, sending to the private data system a return message resolving the identity of the first subject as the selected reference subject and including a first set of combined data attributes representing a resolved first subject, wherein the first set of combined data attributes includes one or more of the first set of query attributes representing the first subject and one or more selected reference data attributes representing the selected reference subject, wherein the return message establishes to the private data system that the first subject, the selected reference subject, and the resolved first subject are all the same subject.

12. The improved method of claim 11 further comprising:

on a condition that the selected reference subject represented by the first set of combined data attributes resolves uniquely with a selected private subject represented by at least one private data record contained in a private database, wherein each private data record in the private database contains one or more private data attributes:

resolving with certainty the identity of the first subject, represented by the first set of query attributes, as the selected private subject by linking, in the private database, the selected private subject with the resolved first subject, represented by the first set of combined data attributes;

storing, in the at least one private data record of the private data system, one or more of the first set of combined data attributes contained within the return message in the at least one private data record; and returning, to a second enterprise, one or more of the first set of combined data attributes.

13. The improved method of claim 11, the method further comprising:

on a condition that the selected reference subject does not resolve uniquely at least one private data record contained in a private database:

generating a new private data record including a new private data record ID attribute;

storing in the new private data record the one or more of the first set of combined data attributes contained in the return message as attributes that resolve uniquely the subject of the new private data record, wherein the subject of the new private data record is the same as the resolved first subject; and returning, to a second enterprise, one or more of the first set of combined data attributes.

14. The method of claim 11, the method further comprising:

on a condition that the first subject does not resolve uniquely with a reference data record contained in the reference database:

sending, to the private data system a return message comprising the first set of query attributes.

15. The method of claim 14, the method further comprising:

on a condition that the first subject, represented by the first set of query attributes, resolves uniquely with a selected private subject represented by one or more selected private data attributes contained in at least one private data record:

storing one or more attributes from the first set of query attributes in the at least one private data record; and returning, to a second enterprise, the one or more selected private data attributes.

16. The method of claim 14, the method further comprising:

on a condition that the first subject, represented by the first set of query attributes, does not resolve uniquely with at least one private data record represented by one or more private attributes contained in a private database:

generating a new private data record including a new private data record ID attribute;

storing in the new private data record the one or more of the first set of query attributes as attributes that resolve uniquely the subject of the new private data record, wherein the subject of the new private data record is the same as the first subject; and returning, to a second enterprise, the new private data record ID attribute.

17. The improved method of claim 11 wherein the one or more selected reference record attributes comprises a reference record ID attribute of the selected reference data record.

18. The improved method of claim 11 wherein the one or more selected reference record attributes consists of a reference record ID attribute of the selected reference data record.

* * * * *